United States Patent [19]
Steck et al.

[11] Patent Number: 5,985,942
[45] Date of Patent: *Nov. 16, 1999

[54] α, β, β-TRIFLUOROSTYRENE-BASED COMPOSITE MEMBRANES

[75] Inventors: Alfred E. Steck, West Vancouver; Charles Stone, Vancouver, both of Canada

[73] Assignee: Ballard Power Systems Inc., Burnaby, Canada

[*] Notice: This patent is subject to a terminal disclaimer.

[21] Appl. No.: 09/186,449

[22] Filed: Nov. 5, 1998

Related U.S. Application Data

[63] Continuation of application No. 08/583,638, Jan. 5, 1996, Pat. No. 5,834,523, which is a continuation-in-part of application No. 08/442,206, May 16, 1995, Pat. No. 5,498,639, which is a continuation of application No. 08/124,924, Sep. 21, 1993, Pat. No. 5,422,411.

[51] Int. Cl.$^6$ .............................. C08J 5/22; C08F 14/18
[52] U.S. Cl. .............................. 521/27; 521/32; 521/33; 521/37; 526/243; 526/251; 526/253; 526/255
[58] Field of Search .................................. 521/27, 32, 33

[56] References Cited

U.S. PATENT DOCUMENTS

| | | | |
|---|---|---|---|
| 3,341,366 | 9/1967 | Hodgdon, Jr. et al. | 136/86 |
| 3,945,927 | 3/1976 | Imai et al. | 210/500 |
| 4,469,564 | 9/1984 | Okinaka et al. | 204/15 |
| 4,650,551 | 3/1987 | Carl et al. | 204/59 R |
| 4,865,930 | 9/1989 | Kindler et al. | 429/192 |
| 5,094,895 | 3/1992 | Branca et al. | 428/36.91 |
| 5,409,785 | 4/1995 | Nakano et al. | 429/33 |
| 5,422,411 | 6/1995 | Wei et al. | 526/243 |
| 5,498,639 | 3/1996 | Wei et al. | 521/27 |
| 5,547,551 | 8/1996 | Bahar et al. | 204/296 |
| 5,834,523 | 11/1998 | Steck | 521/27 |

FOREIGN PATENT DOCUMENTS

| | | |
|---|---|---|
| 3-232529 | 10/1991 | Japan. |
| 6-29032 | 2/1994 | Japan. |

OTHER PUBLICATIONS

Kolde, et al., "Advanced Composite Polymer electrolyte Fuel Cell Membranes," *Electrochemical Society Proceedings*, 95–23:193–201 (Oct., 1995).

Nikitina, "αββ–Trifluorostyrene and polymers based on it," *Russian Chemical Reviews* 59(6):575–589 (1990).

Penner, et al., "Electronically Conductive Composite Polymer Membrane," *J. Electrochem. Soc.*, 133(2):310–315 (Feb., 1986).

Penner, et al., "Ion Transporting composite Membranes," *J. Electrochem. Soc.*, 132(2):514–515 (1985).

Taylor, et al., "Characteristics of Supported Cation Exchange Membranes for Chlor–Alkali applications," proceedings from a meeting of the Electrochemical society (May 4–9, 1986).

Taylor, et al., "The Effect of Support Morphology on composite Membrane Performance," proceedings from a meeting of The Electrochemical Society (Oct. 19–24, 1986).

Verbrugge, et al., "Composite Membranes for Fuel–Cell Applications," *AIChE Journal* 38(1):93–100 (Jan., 1992).

*Primary Examiner*—Fred Zitomer
*Attorney, Agent, or Firm*—McAndrews, Held & & Malloy, Ltd.

[57] ABSTRACT

A composite membrane is provided in which a porous substrate is impregnated with a polymeric composition comprising various combinations of α,β,β-trifluorostyrene, substituted α,β,β-trifluorostyrene and ethylene-based monomeric units. Where the polymeric composition includes ion-exchange moieties, the resultant composite membranes are useful in electrochemical applications, particularly as membrane electrolytes in electrochemical fuel cells.

32 Claims, 3 Drawing Sheets

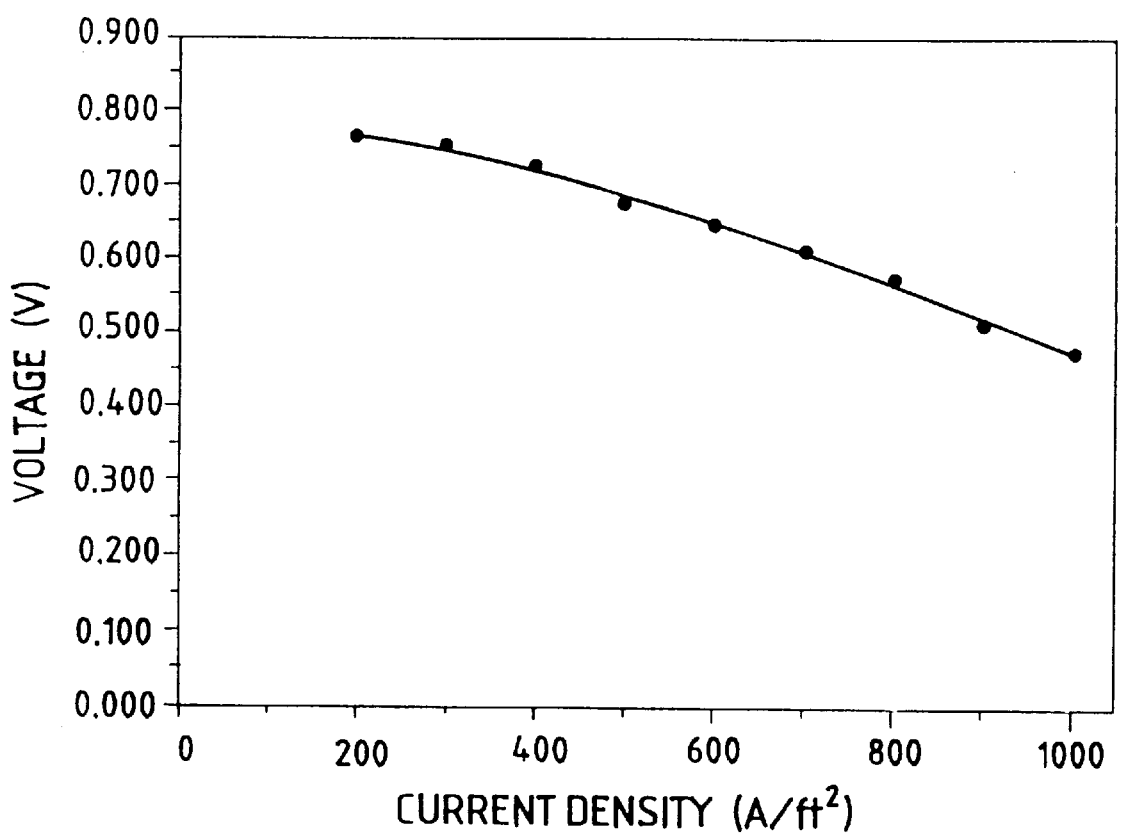

α, β, β-TRIFLUOROSTYRENE-BASED COMPOSITE MEMBRANES

CROSS-REFERENCE TO RELATED APPLICATIONS

This application is a continuation of U.S. Patent Application Ser. No. 08/583,638 filed Jan. 5, 1996, now U.S. Pat. No. 5,834,523 issued Nov. 10, 1998, which is a continuation-in-part of U.S. Patent Application Ser. No. 08/442,206 filed May 16, 1995, now U.S. Pat. No. 5,498,639 issued Mar. 12, 1996, which is a continuation of U.S. Patent Application Ser. No. 08/124,924 filed Sep. 21, 1993, now U.S. Pat. No. 5,422,411 issued Jun. 6, 1995, entitled "Trifluorostyrene and Substituted Trifluorostyrene Copolymeric Compositions and Ion-exchange Membranes Formed Therefrom". The '638, '206 and '924 applications, incorporated herein by reference in their entireties, describe polymeric compositions, as well as composite membranes thereof, derived from copolymers of α,β,β-trifluorostyrene with a variety of substituted α,β,β-trifluorostyrenes. These compositions are suitable for use as membranes, particularly as ion-exchange membranes. This application is also related to U.S. Patent Application Ser. No. 08/480,098 filed Jun. 6, 1995, entitled "Substituted Trifluorostyrene Compositions". The latter application, which is also incorporated herein by reference in its entirety, describes copolymers of α,β,β-trifluorostyrene and substituted α,β,β-trifluorostyrenes, including sulfonyl fluoride substituted α,β,β-trifluorostyrene monomeric units that are conveniently hydrolyzed to produce polymeric compositions with ion-exchange moieties. This application is further related to U.S. Patent Application Ser. No. 08/482,948 filed Jun. 7, 1995, entitled "Copolymeric Compositions of Trifluorostyrene, Substituted Trifluorostyrene and Substituted Ethylene, and Ion-exchange Membranes Formed Therefrom". The latter application, which is also incorporated herein by reference in its entirety, describes copolymers of α,β,β-trifluorostyrene and substituted α,β,β-trifluorostyrenes with substituted ethylene monomeric units. These compositions are suitable for use as membranes, particularly as ion-exchange membranes.

FIELD OF THE INVENTION

This invention relates generally to composite membranes comprising a porous substrate and a polymeric composition comprising various combinations of α,β,β-trifluorostyrene, substituted α,β,β-trifluorostyrene and ethylene-based monomeric units. Where the polymeric composition includes ion-exchange moieties, the resultant composite membranes are useful in electrochemical applications, particularly as membrane electrolytes in electrochemical fuel cells.

BACKGROUND OF THE INVENTION

Dense films can be obtained from solutions of poly-α,β,β-trifluorostyrene. However, the brittleness of these films greatly limits their application. Films obtained from some sulfonated poly-α,β,β-trifluorostyrenes can be used as ion-exchange membranes. However, such films often have unfavorable mechanical properties when wet, and are known to be very brittle in the dry state (see, for example, Russian Chemical Reviews, Vol. 59, p. 583 (1988)). Such films are of little practical use in fuel cells due to their poor physical properties. Some improvements in mechanical properties have been achieved by blending sulfonated poly-α,β,β-trifluorostyrene with polyvinylidene fluoride and triethyl phosphate plasticizer, but these films remained unsatisfactory for application in electrochemical cells (see Fuel Cell Handbook, A. J. Appleby, published by Van Nostrand Reinhold, p. 286 (1989)).

U.S. Pat. No. 5,422,411 and the related patent applications mentioned above describe various polymeric compositions incorporating substituted α,β,β-trifluorostyrenes and some cases further incorporating substituted ethylenes. Typically these compositions, as membranes, possess favorable mechanical properties compared to poly-α,β,β-trifluorostyrene and sulfonated poly-α,β,β-trifluorostyrene, although some of the membranes have a tendency to become brittle in the fully dehydrated state, depending, for example, on the equivalent weight. This effect is most apparent at equivalent weights below approximately 380 g/mol. Ion-exchange membranes derived from these polymeric compositions are suitable for many applications, including use in electrochemical applications, such as fuel cells.

For ease of handling, for example, in the preparation of membrane electrode assemblies for use in electrochemical fuel cells, the mechanical strength of the membrane in the dry state is important. In electrochemical applications, such as electrolytic cells and fuel cells, the dimensional stability (changes in the dimensions of the membrane due to changes in the degree of hydration) of the membrane during operation is also important. However, to improve performance, it is generally desirable to reduce membrane thickness and to decrease the equivalent weight (thereby increasing the water content) of the membrane electrolyte, both of which tend to decrease both the mechanical strength in the dry state and the dimensional stability in the wet state. One way to improve mechanical strength and dimensional stability in ionomeric membranes is through use of a substrate or support material, to give a composite membrane. The substrate is selected so that it imparts mechanical strength and dimensional stability to the membrane. The substrate material can be combined with the membrane polymeric material to form a composite membrane in a variety of ways. For example, if possible, an unsupported membrane can be preformed and then laminated to the porous substrate. Alternatively, a solution of the polymer can be impregnated into the porous substrate material, and the composite membrane subsequently dried. The formation of composite membranes via impregnation provides a more intimate contact between the two components, thus giving advantages over standard lamination approaches.

Composite ion-exchange membranes prepared by impregnating commercially available porous polytetrafluoroethylene film (Gore-tex®) with Nafion®, a perfluorosulfonate ionomer, have been described in Journal of the Electrochemical Society, Vol. 132, pp. 514–515 (1985). The major goal in the study was to develop a composite membrane with the desirable chemical and mechanical features of Nafion®, but which could be produced at low cost. Indeed, based on the polymer loadings necessary to produce these composite membranes, they are a low cost alternative to the costly perfluorosulfonic acid membranes. As indicated above, however, these perfluorosulfonate ionomers are known to form membranes suitable for use in electrochemical applications without the use of a substrate.

It has been discovered that polymers which have a tendency to become brittle in the dehydrated state can be rendered mechanically stable, even in the fully dehydrated state, by impregnation into suitable substrates.

Furthermore, it has been discovered that even polymers which are poor film formers, or polymers which form films with mechanical properties and dimensional stability which would preclude their use in electrochemical and other applications, can be made into composite membranes through incorporation into a suitable substrate. The resulting composite membranes have the desired physical properties for use in a wide range of applications.

SUMMARY OF THE INVENTION

In one aspect of the present invention, a composite membrane comprises a porous substrate impregnated with a polymeric composition comprising α,β,β-trifluorostyrene monomeric units.

In another aspect, a composite membrane comprises a porous substrate impregnated with a polymeric composition comprising substituted α,β,β-trifluorostyrene monomeric units. Substituted α,β,β-trifluorostyrene monomeric units have at least one non-hydrogen substituent on the aromatic ring. In a preferred embodiment, the polymeric composition comprises at least two different substituted α,β,β-trifluorostyrene monomeric units.

In a first embodiment of a composite membrane comprising a porous substrate impregnated with a polymeric composition comprising α,β,β-trifluorostyrene monomeric units, the polymeric composition further comprises ethylene monomeric units, the polymeric composition derived from a copolymerization reaction involving at least ethylene and α,β,β-trifluorostyrene.

In a second embodiment of a composite membrane comprising a porous substrate impregnated with a polymeric composition comprising α,β,β-trifluorostyrene monomeric units, the polymeric composition further comprises partially fluorinated ethylene monomeric units, the polymeric composition derived from a copolymerization reaction involving at least α,β,β-trifluorostyrene and, for example, $CH_2=CHF$, $CHF=CHF$, $CF_2=CH_2$, or $CF_2=CHF$.

In a third embodiment of a composite membrane comprising a porous substrate impregnated with a polymeric composition comprising α,β,β-trifluorostyrene monomeric units, the polymeric composition further comprises tetrafluoroethylene monomeric units, the polymeric composition derived from a copolymerization reaction involving at least tetrafluoroethylene and α,β,β-trifluorostyrene.

In a fourth embodiment of a composite membrane comprising a porous substrate impregnated with a polymeric composition comprising α,β,β-trifluorostyrene monomeric units, the polymeric composition further comprises:

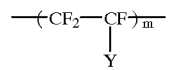

here m is an integer greater than zero; Y is selected from the group consisting of chlorine, bromine, iodine, $C_xH_yF_z$ (where x is an integer greater than zero and y+z=2x+1), O—R (where R is selected from the group consisting of $C_xH_yF_z$ (where x is an integer greater than zero and y+z=2x+1) and aryls), $CF=CF_2$, ON, COOH and $CO_2R^1$ (where $R^1$ is selected from the group consisting of perfluoroalkyls, aryls, and $NR^2R^3$ where $R^2$ and $R^3$ are selected from the group consisting of hydrogen, alkyls and aryls).

In a fifth embodiment of a composite membrane comprising a porous substrate impregnated with a polymeric composition comprising α,β,β-trifluorostyrene monomeric units, the polymeric composition further comprises styrene monomeric units, the polymeric composition derived from a copolymerization reaction involving at least styrene and α,β,β-trifluorostyrene.

In a sixth embodiment of a composite membrane comprising a porous substrate impregnated with a polymeric composition comprising α,β,β-trifluorostyrene monomeric units, the polymeric composition further comprises substituted styrene monomeric units, the polymeric composition derived from a copolymerization reaction involving at least a substituted styrene and α,β,β-trifluorostyrene. Substituted styrene monomeric units have at least one non-hydrogen substituent on the aromatic ring.

In a first embodiment of a composite membrane comprising a porous substrate impregnated with a polymeric composition comprising substituted α,β,β-trifluorostyrene monomeric units, the polymeric composition comprises:

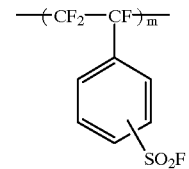

where m is an integer greater than zero. In a further embodiment the polymeric composition comprises:

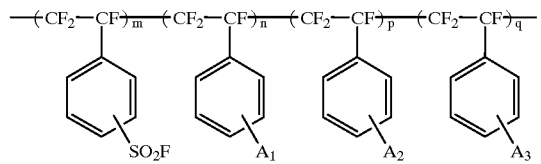

where m is an integer greater than zero, and at least one of n, p and q is an integer greater than zero; $A_1$, $A_2$, and $A_3$ are selected from the group consisting of hydrogen, halogens, $C_xH_yF_z$ (where x is an integer greater than zero and y+z=2x+1), $CF=CF_2$, CN, $NO_2$ and OH, O—R (where R is selected from the group consisting of alkyls and perfluoroalkyls and aryls). In a still further embodiment, the group from which $A_1$, $A_2$, and $A_3$ are selected further consists of $SO_3H$, $PO_2H_2$, $PO_3H_2$, $CH_2PO_3H_2$, COOH, $OSO_3H$, $OPO_2H_2$, $OPO_3H_2$, $NR_3^+$ (where R is selected from the group consisting of alkyls, perfluoroalkyls and aryls) and $CH_2NR_3^+$ (where R is selected from the group consisting of alkyls, perfluoroalkyls and aryls), and at least one of $A_1$, $A_2$ and $A_3$ is selected from the group consisting of $SO_3H$, $PO_2H_2$, $PO_3H_2$, $CH_2PO_3H_2$, COOH, $OSO_3H$, $OPO_2H_2$, $OPO_3H_2$, $NR_3^+$ (where R is selected from the group consisting of alkyls, perfluoroalkyls and aryls) and $CH_2NR_3^+$ (where R is selected from the group consisting of alkyls, perfluoroalkyls and aryls).

In a second embodiment of a composite membrane comprising a porous substrate impregnated with a polymeric composition comprising substituted α,β,β-trifluorostyrene monomeric units, the polymeric composition comprises:

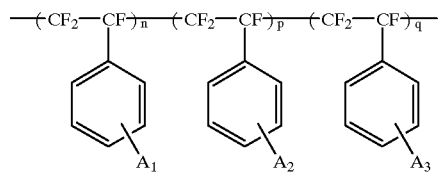

where at least one of n, p and q is an integer greater than zero; $A_1$, $A_2$ and $A_3$ are selected from the group consisting of $CF=CF_2$, CN, $NO_2$ and OH, O—R (where R is selected from the group consisting of $C_xH_yF_z$ (where x is an integer greater than three and y+z=2x+1) and aryls).

In a third embodiment of a composite membrane comprising a porous substrate impregnated with a polymeric composition comprising substituted α,β,β-trifluorostyrene monomeric units, the polymeric composition comprises:

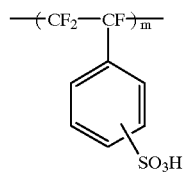

where m is an integer greater than zero.

In a fourth embodiment of a composite membrane comprising a porous substrate impregnated with a polymeric composition comprising substituted α,β,β-trifluorostyrene monomeric units, the polymeric composition comprises:

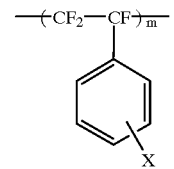

where m is an integer greater than zero; X is selected from the group consisting of $PO_2H_2$, $PO_3H_2$, $CH_2PO_3H_2$, COOH, $OSO_3H$, $OPO_2H_2$, $OPO_3H_2$, $OArSO_3H$ where Ar is an aryl, $NR_3^+$ (where R is selected from the group consisting of alkyls, perfluoroalkyls and aryls) and $CH_2NR_3^+$ (where R is selected from the group consisting of alkyls, perfluoroalkyls and aryls).

In a fifth embodiment of a composite membrane comprising a porous substrate impregnated with a polymeric composition comprising substituted α,β,β-trifluorostyrene monomeric units, the polymeric composition comprises:

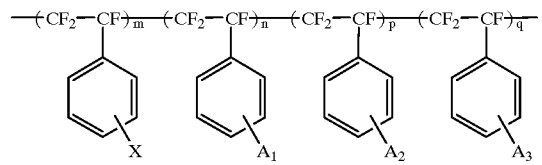

where m is an integer greater than zero, and at least one of n, p and q is an integer greater than zero; X is selected from the group consisting of $SO_3H$, $PO_2H_2$, $PO_3H_2$, $CH_2PO_3H_2$, COOH, $OSO_3H$, $OPO_2H_2$, $OPO_3H_{21}$ $OArSO_3H$ where Ar is an aryl, $NR_3^+$ (where R is selected from the group consisting of alkyls, perfluoroalkyls and aryls) and $CH_2NR_3^+$ (where R is selected from the group consisting of alkyls, perfluoroalkyls and aryls); $A_1$, $A_2$ and $A_3$ are selected from the group consisting of halogens, $C_xH_yF_z$ (where x is an integer greater than zero and y+z=2x+1), $CF=CF_2$, CN, $NO_2$ and OH, O—R (where R is selected from the group consisting of alkyls and perfluoroalkyls and aryls). In a further embodiment, the group from which $A_1$, $A_2$ and $A_3$ are selected further consists of hydrogen. In a still further embodiment, the group from which $A_1$, $A_2$ and $A_3$ are selected further consists of $SO_3H$, $PO_2H_2$, $PO_3H_2$, $CH_2PO_3H_2$, COOH, $OSO_3H$, $OPO_2H_2$, $OPO_3H_2$, $NR_3^+$ (where R is selected from the group consisting of alkyls, perfluoroalkyls and aryls) and $CH_2NR_3^+$(where R is selected from the group consisting of alkyls, perfluoroalkyls and aryls), and at least one of $A_1$, $A_2$ and $A_3$ is selected from the group consisting of $SO_3H$, $PO_2H_2$, $PO_3H_2$, $CH_2PO_3H_2$, COOH, $OSO_3H$, $OPO_2H_2$, $OPO_3H_2$, $NR_3^+$ (where R is selected from the group consisting of alkyls, perfluoroalkyls and aryls) and $CH_2NR_3^+$ (where R is selected from the group consisting of alkyls, perfluoroalkyls and aryls).

In a sixth embodiment of a composite membrane comprising a porous substrate impregnated with a polymeric composition comprising substituted α,β,β-trifluorostyrene monomeric units, the polymeric composition comprises:

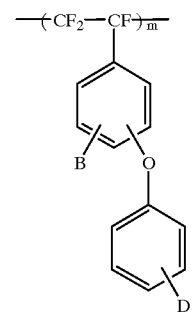

where m is an integer greater than zero; B and D are selected from the group consisting of hydrogen, $SO_2F$, $SO_3H$, $PO_2H_2$, $PO_3H_2$, $CH_2PO_3H_2$, COOH, $OSO_3H$, $OPO_2H_2$, $OPO_3H_2$, $NR_3^+$ (where R is selected from the group consisting of alkyls, perfluoroalkyls and aryls) and $CH_2NR_3^+$ (where R is selected from the group consisting of alkyls, perfluoroalkyls and aryls). In a further embodiment, the polymeric composition comprises:

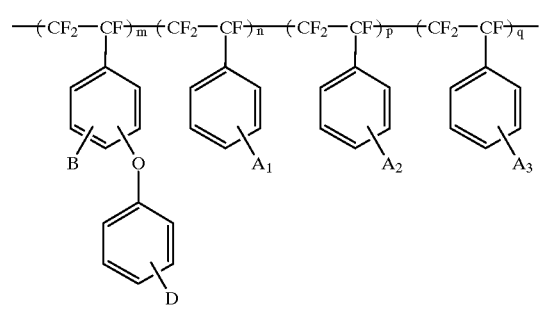

where m is an integer greater than zero, and at least one of n, p and q is an integer greater than zero; B and D are selected from the group consisting of hydrogen, $SO_2F$, $SO_3H$, $PO_2H_{21}$ $PO_3H_2$, $CH_2PO_3H_2$, COOH, $OSO_3H$, $OPO_2H_2$, $OPO_3H_2$, $NR_3^-$(where R is selected from the group consisting of alkyls, perfluoroalkyls and aryls) and $CH_2NR_3^+$ (where R is selected from the group consisting of alkyls, perfluoroalkyls and aryls); $A_1$, $A_2$ and $A_3$ are selected from the group consisting of hydrogen, $SO_2F$, halogens, $C_xH_yF_z$ (where x is an integer greater than zero and y+z=2x+1), $CF=CF_2$, CN, $NO_2$ and OH, O—R (where R is selected from the group consisting of alkyls and perfluoroalkyls and aryls). In a still further embodiment, the group from which $A_1$, $A_2$ and $A_3$ are selected further consists of $SO_3H$, $PO_2H_2$, $PO_3H_2$, $CH_2PO_3H_2$, COOH, $OSO_3H$, $OPO_2H_2$, $OPO_3H_2$, $NR_3^+$ (where R is selected from the group consisting of alkyls, perfluoroalkyls and aryls) and $CH_2NR_3^+$ (where R is selected from the group consisting of alkyls, perfluoroalkyls and aryls), and at least one of $A_1$, $A_2$ and $A_3$ is selected from the group consisting of $SO_3H$, $PO_2H_2$, $PO_3H_2$, $CH_2PO_3H_2$, COOH, $OSO_3H$, $OPO_2H_2$, $OPO_3H_2$, $NR_3^+$ (where R is selected from the group consisting of alkyls, perfluoroalkyls and aryls) and $CH_2NR_3^+$ (where R is selected from the group consisting of alkyls, perfluoroalkyls and aryls). In preferred embodiments B is hydrogen.

In a seventh embodiment of a composite membrane comprising a porous substrate impregnated with a polymeric composition comprising substituted $\alpha,\beta,\beta$-trifluorostyrene monomeric units, the polymeric composition further comprises ethylene monomeric units.

In an eighth embodiment of a composite membrane comprising a porous substrate impregnated with a polymeric composition comprising substituted $\alpha,\beta,\beta$-trifluorostyrene monomeric units, the polymeric composition further comprises partially fluorinated ethylene monomeric units, the polymeric composition derived from a copolymerization reaction involving, for example, $CH_2=CHF$, $CHF=CHF$, $CF_2=CH_2$, or $CF_2=CHF$.

In a ninth embodiment of a composite membrane comprising a porous substrate impregnated with a polymeric composition comprising substituted $\alpha,\beta,\beta$-trifluorostyrene monomeric units, the polymeric composition further comprises tetrafluoroethylene monomeric units.

In a tenth embodiment of a composite membrane comprising a porous substrate impregnated with a polymeric composition comprising substituted $\alpha,\beta,\beta$-trifluorostyrene monomeric units, the polymeric composition further comprises:

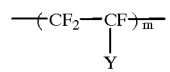

where m is an integer greater than zero; Y is selected from the group consisting of chlorine, bromine, iodine, $C_xH_yF_z$ (where x is an integer greater than zero and $y+z=2x+1$), O—R (where R is selected from the group consisting of $C_xH_yF_z$ (where x is an integer greater than zero and $y+z=2x+1$) and aryls), $CF=CF_2$, CN, COOH and $CO_2R^1$ (where $R^1$ is selected from the group consisting of alkyls, perfluoroalkyls, aryls, and $NR^2R^3$ where $R^2$ and $R^3$ are selected from the group consisting of hydrogen, alkyls and aryls).

In an eleventh embodiment of a composite membrane comprising a porous substrate impregnated with a polymeric composition comprising substituted $\alpha,\beta,\beta$-trifluorostyrene monomeric units, the polymeric composition further comprises styrene monomeric units.

In a twelfth embodiment of a composite membrane comprising a porous substrate impregnated with a polymeric composition comprising substituted $\alpha,\beta,\beta$-trifluorostyrene monomeric units, the polymeric composition further comprises substituted styrene monomeric units. Substituted styrene monomeric units have at least one non-hydrogen substituent on the aromatic ring.

In the aspects and embodiments described above, the substrate is preferably a porous film or sheet material. For electrochemical applications, for example, preferred porous substrates comprise, or consist essentially of, porous polyolefins. Preferred polyolefins are polyethylene and polypropylene. Particularly preferred substrates comprise, or consist essentially of, porous polytetrafluoroethylene, also known as expanded polytetrafluoroethylene.

In a preferred aspect, a composite membrane comprises a porous substrate impregnated with a polymeric composition comprising:

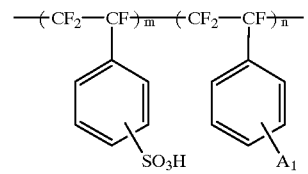

where m and n are integers greater than zero and $A_1$ is selected from the group consisting of fluorine, $CF_3$ and para-phenoxy. In a further embodiment of this preferred aspect, the group from which $A_1$ is selected further consists of hydrogen.

In another preferred aspect, a composite membrane comprises a porous substrate impregnated with a polymeric composition comprising:

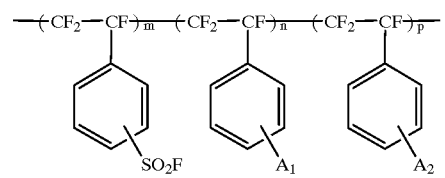

where m, n, and p are integers greater than zero and $A_1$ and $A_2$ are selected from the group consisting of hydrogen, fluorine, $CF_3$, and para-phenoxy.

In another preferred aspect, a composite membrane comprises a porous substrate impregnated with a polymeric composition comprising:

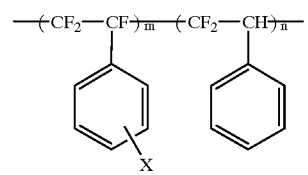

where m and n are integers greater than zero and X is selected from the group consisting of para-$SO_2F$, meta-$SO_3H$ and para-$SO_3H$.

In yet another preferred aspect, a composite membrane comprises a porous substrate impregnated with a polymeric composition comprising:

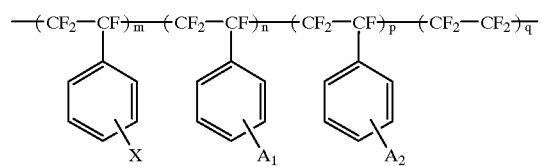

where m and q are integers greater than zero, n and p are zero or an integer greater than zero; X is selected from the group consisting of para-$SO_2F$, meta-$SO_3H$ and para-$SO_3H$; and $A_1$ and $A_2$ are selected from the group consisting of hydrogen, fluorine, $CF_3$, and para-phenoxy. In a further embodiment of this preferred aspect, n is an integer greater than zero.

In still another preferred aspect, a composite membrane comprises a porous substrate impregnated with a polymeric composition comprising:

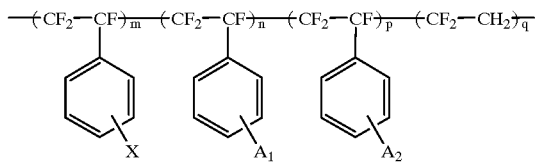

where m and q are integers greater than zero, n and p are zero or an integer greater than zero; X is selected from the group consisting of para-$SO_2F$, meta-$SO_3H$ and para-$SO_3H$; and $A_1$ and $A_1$ are selected from the group consisting of hydrogen, fluorine, $CF_3$, and para-phenoxy. In a further embodiment of this preferred aspect, n is an integer greater than zero.

In the aspects and embodiments described above, the polymeric compositions can consist essentially of the described monomeric units.

In all of the above preferred aspects, preferably the porous substrate comprises polytetrafluoroethylene. A preferred porous substrate consists essentially of polytetrafluoroethylene.

In the aspects and embodiments described above, the $A_1$, $A_2$, $A_3$ substituents may be further elaborated by known means such as, for example, by hydrolysis of the CN group to form COOH or by reduction with common reducing agents (such as, for example, Raney nickel) to form a primary amine, thereby transforming the $A_1$, $A_2$ and $A_3$ substituents into ion-exchange moieties. The resulting polymeric composition may thus comprise one or more type of ion-exchange moiety, and may also comprise both cation-exchange and anion-exchange moieties.

The term "monomeric unit" as used herein indicates that the polymeric composition contains the described fragment or unit, and is obtained by a polymerization reaction involving the corresponding unsaturated monomer.

The substituents on the aromatic rings (including, for example, $A_1$, $A_2$, $A_3$, X, B and D) may each be located in the ortho, meta or para positions, as indicated in the formulas wherein the chemical bond drawn for the substituents intersects the aromatic ring. In preferred aspects of the described embodiments, the substituents are in the meta or para positions.

As used herein, the term "aryl" refers to a substituted or unsubstituted phenyl group. The formula $C_xH_yF_z$ (where x is an integer greater than zero and y+z=2x+1) is used to indicate alkyl, perfluoroalkyl or partially fluorinated alkyl groups.

In accordance with convention in the art, the above chemical formulas for polymeric compositions containing more than two monomeric units (where at least three of m, n, p and q are greater than zero) are intended to indicate that the monomeric units are present in the polymeric composition, but are not limited to the particular order in which the monomeric units are set forth in each general formula. For example, random linear copolymers, alternating copolymers and linear block copolymers, formed from the indicated monomeric units, are contemplated.

BRIEF DESCRIPTION OF THE DRAWINGS

FIG. 5 is a plot of cell voltage as a function of current density in an electrochemical fuel cell employing a composite membrane of expanded polytetrafluoroethylene impregnated with a low equivalent weight sulfonated copolymer of $\alpha,\beta,\beta$-trifluorostyrene and m-trifluoromethyl-$\alpha,\beta,\beta$-trifluorostyrene, as the proton exchange membrane.

DETAILED DESCRIPTION OF THE PREFERRED EMBODIMENTS

Figure 1:
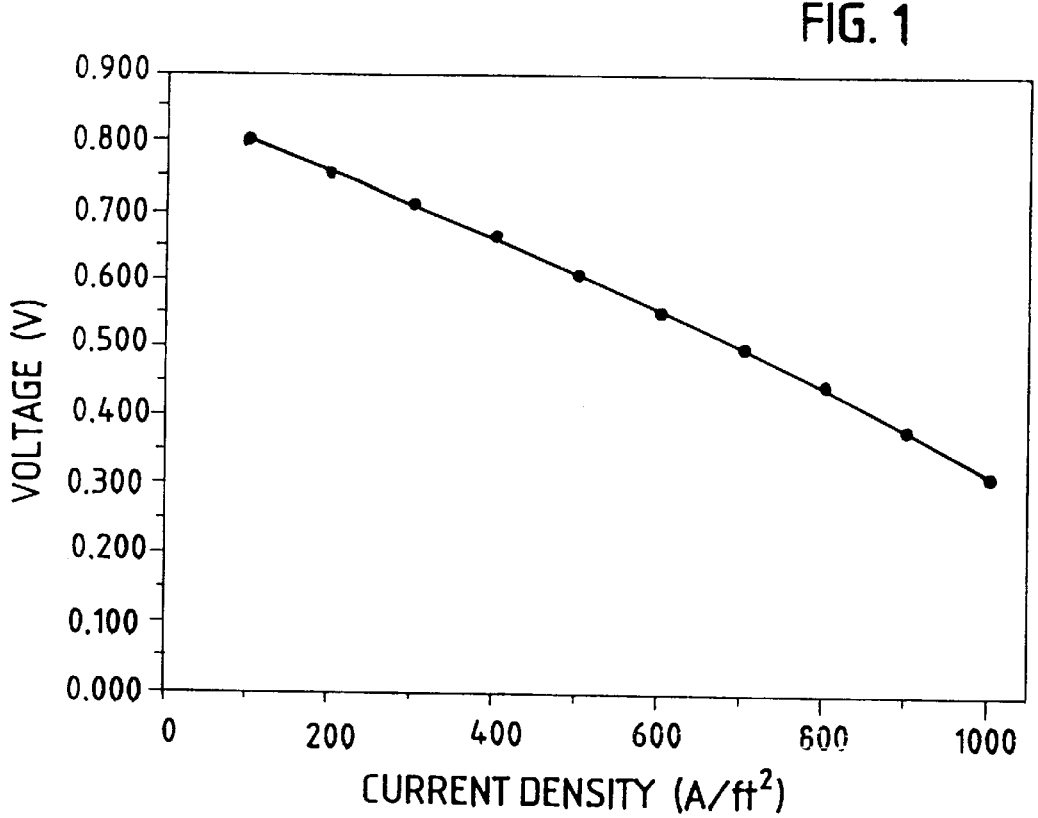
FIG. 1 is a plot of cell voltage as a function of current density (expressed in amperes per square foot or "ASF") in an electrochemical fuel cell employing a composite membrane of porous polyethylene impregnated with a sulfonated copolymer of $\alpha,\beta,\beta$-trifluorostyrene and m-trifluoromethyl-$\alpha,\beta,\beta$-trifluorostyrene, as the proton exchange membrane.

Methods for preparing the polymeric compositions described herein are described in the related applications or will be apparent to those skilled in the art.

The preferred substrate material is dependent on the application in which the composite membrane is to be used. The substrate material preferably has good mechanical properties, is chemically and thermally stable in the environment in which the composite membrane is to be used, is tolerant of the solvent used for impregnation, and in most applications is preferably flexible. For example, the porous substrate can be a woven or nonwoven fabric or cloth, or can be made of paper, fiber glass, cellulosics or a ceramic material. Preferred substrates for electrochemical applications are porous polymeric materials. Preferred polymeric materials are, for example, hydrocarbons such as porous polyolefins, especially polyethylene and polypropylene. In some applications, a perfluorinated polymeric substrate may be preferred, for example, a preferred substrate material, when the composite membrane is to be used in an electrochemical fuel cell, is porous polytetrafluoroethylene, also known as expanded polytetrafluoroethylene. Porous polyolefins and polytetrafluoroethylenes typically have excellent mechanical strength, flexibility and do not swell in water. Polytetrafluoroethylene offers additional advantages in that it is also chemically inert, and porous polytetrafluoroethylene films with different characteristics are commercially available from various sources. It may be possible to obtain or prepare other suitable porous polymeric substrates from, such as, for example, polyvinylidene fluoride or polysulfones. Copolymeric substrates such as, for example, poly(ethylene-co-tetrafluoroethylene) and poly(tetrafluoroethylene-co-hexafluoropropylene), may also be used.

The degree of porosity, pore size and thickness of the substrate used in the composite membrane can be selected to suit the application. For use of the composite membrane as an electrolyte in an electrochemical fuel cell, the substrate thickness is preferably 10–200 μm, and more preferably 25–50 μm, the preferable average pore diameter is 0.1–1.0 μm, and the preferable porosity is 50–98%, more preferably 75–90%.

Depending on the application the resultant composite membrane may be gas permeable or gas impermeable. The loading of the polymeric composition on the substrate can be varied in order to control the porosity of the resultant composite membrane. For fuel cell applications, the composite membrane is preferably substantially gas impermeable, thus the degree of impregnation and loading is such that the porosity of the composite membrane is reduced essentially to zero.

In a method for preparing composite membranes, the polymeric composition is dissolved in a solvent, typically an organic solvent, to form a solution. The solvent used will depend, for example, on both the nature of the polymeric composition and the substrate. For impregnation of porous polyolefins with the type of polymeric compositions described herein, suitable solvents include N,N-dimethylformamide, N-methylpyrrolidone, dimethylsulfoxide and N,N-dimethylacetamide. When polytetrafluoroethylene is the substrate, an alcohol or mixture of alcohols (chosen, for example, from methanol, ethanol and propan-2-ol) is often the preferred solvent. The concentration of the solution will depend on the loading desired, and whether the composite membrane is to be porous or not. For example, if the composite membrane is to be gas permeable a lower concentration is generally preferred.

The porous substrate is then impregnated, for example, by constraining the substrate in a frame and dipping or soaking it in the solution. The contact time is dependent on the viscosity and percentage solids of the solution. Other techniques known in the art, such as ultrasonication, may be used to facilitate impregnation. Also, multiple impregnations, possibly with different polymeric compositions, may be desirable for some applications. The substrate is then removed from the solution and the composite membrane dried preferably in a humidity controlled atmosphere (generally at less than or equal to 2% relative humidity) at above ambient temperatures.

If the composite membrane includes proton-exchange moieties and is to be used in, for example, a proton-exchange membrane fuel cell, it is removed from the frame, treated with 1 M hydrochloric acid and washed with deionized water prior to use.

The means by which the process described above could be modified for impregnation of non-membrane substrates, and also for a continuous composite membrane manufacturing process will be apparent to those skilled in the art.

In the preparation of composite ion-exchange membranes, the ion-exchange moieties can be:

(i) present in the polymeric composition prior to its impregnation into the substrate; or (ii) introduced post-impregnation through further reaction of the polymeric composition on the substrate; or (iii) introduced via conversion of precursor groups, present in the polymeric composition, after impregnation.

If the ion-exchange moieties are to be introduced via a post-impregnation conversion or reaction, the substrate needs to selected such that it can withstand the post-impregnation treatment step. For example, in post-impregnation introduction of ion-exchange moieties, the ion-exchange moieties may be introduced into polymeric compositions containing unsubstituted $\alpha,\beta,\beta$-trifluorostyrene units (so called "base polymers") via aromatic substitution of at least a portion of those units, after preparation of a composite membrane. For example, pendant unsubstituted phenyl rings in the composite membrane can be conveniently sulfonated (see U.S. Pat. No. 5,422,411) to produce a composite cation-exchange membrane. Similarly, such pendant unsubstituted phenyl rings may be phosphorylated, carboxylated, quaternary-aminoalkylated or chloromethylated, and further modified to include $-CH_2PO_3H_2$, $-CH_2NR_3^+$ where R is an alkyl, or $-CH_2NAr_3^+$ (where Ar is a substituted or unsubstituted phenyl group) and other substituents, to provide cation-exchange or anion-exchange composite membranes. Further still, the pendent phenyl moiety may contain a hydroxyl group which can be elaborated by known methods to generate $-OSO_3H$, $-OPO_2H_2$ and $-OPO_3H_2$ cation-exchange sites on the composite membrane.

The approach in which the ion-exchange functionality is introduced post-impregnation via conversion of a precursor using simple post-impregnation procedure, such as hydrolysis, can be advantageous. For example, composite membranes comprising polymers containing sulfonyl fluoride moieties ($-SO_2F$) can be hydrolyzed to generate $-SO_3H$ cation-exchange sites. In a typical hydrolysis reaction, the sulfonyl fluoride is converted to the free sulfonic acid functionality by treatment of the composite membrane with concentrated aqueous alkali metal hydroxide at elevated temperatures. This and other procedures for the hydrolysis of $-SO_2F$ to $-SO_3H$ are well-known to those skilled in the art. The latter approach to the introduction of $-SO_3H$ moieties offers advantages over sulfonation of a base polymer in the composite membrane. For example, it permits greater control over the ion-exchange capacity of the resultant composite membrane.

Membranes including sulfonyl fluoride substituted $\alpha,\beta,\beta$-trifluorostyrene monomeric units are described in a related application. Unsupported membranes containing a significant proportion of sulfonyl fluoride substituted $\alpha,\beta,\beta$-trifluorostyrene monomeric units can be very fragile. The mechanical properties of these precursor ion-exchange membranes can be significantly enhanced through incorporation into a porous substrate.

It may be advantageous to introduce ion-exchange moieties after preparation of the composite membranes, as described in (ii) and (iii) above. For example, in electrochemical applications where the preferred substrates are typically hydrophobic, the preparation of a composite membrane by first impregnating the substrate with a solution of a non-ionic polymer which is also essentially hydrophobic may lead to more facile and improved impregnation.

The following examples are for purposes of illustration and are not intended to limit the invention. Examples 1–3 describe the preparation of composite ion-exchange membranes in which porous, high density polyethylene is used as the substrate. Examples 4 and 5 describe the preparation of composite ion-exchange membranes in which expanded polytetrafluoroethylene is used as the porous substrate. In Examples 1, 2, 4 and 5 the ion-exchange moieties were present in the polymeric composition prior to its impregnation into the substrate. In Example 3 the ion-exchange moiety was generated by hydrolysis of sulfonyl fluoride moieties after preparation of the composite membrane. Example 6 sets forth the procedure used to test the composite ion-exchange membranes, prepared as described in Examples 1–5, as membrane electrolytes in an electrochemical fuel cell.

EXAMPLE 1

Porous Polyethylene Impregnated with a Sulfonated Copolymer of α,β,β-trifluorostyrene and m-trifluoromethyl-α,β,β-trifluorostyrene (Composite Membrane A)

The substrate, a 9 inch×9 inch piece of high density polyethylene (obtained from 3M, product ID #43-9100-6770-1, 81% porosity, approximately 50 micron) was clamped in a frame and immersed in a N,N-dimethylformamide solution (7% w/w) of a sulfonated copolymer of α,β,β-trifluorostyrene and m-trifluoromethyl-α,β,β-trifluorostyrene (equivalent weight 384 g/mol) in a glass container. The container was covered to exclude moisture and particulate contaminants. After 1 hour excess polymer solution was removed and the transparent, wetted substrate was placed to dry in a chamber at approximately 2% relative humidity, at 50° C. After approximately 3 hours the dry composite membrane, now opaque, was a mechanically strong flexible film. On immersion in 1 M hydrochloric acid (to ensure protonation of all the sulfonic acid moieties), and subsequent washing with deionized water, the composite membrane once again became transparent. The wet composite membrane (50–60 micron thick) was also strong and flexible.

EXAMPLE 2

Porous Polyethylene Impregnated with Sulfonated poly-α,β,β-trifluorostyrene (Composite Membrane B)

The substrate, a 10 inch×10 inch piece of high density polyethylene (from 3M, product ID #43-9100-6770-1, 81% porosity, 50 micron) was clamped in a frame and immersed in a N,N-dimethylformamide solution (7% w/w) of a sulfonated polymer of α,β,β-trifluorostyrene (equivalent weight 430 g/mol) in a glass container. The container was covered to exclude moisture and particulate contaminants. After 2 hours excess polymer solution was removed and the transparent, wetted substrate was placed to dry in a chamber at approximately 2% relative humidity, at 50° C. After approximately 3 hours the dry composite membrane, now opaque, was a mechanically strong flexible film, in contrast to the analogous unsupported membrane which would be extremely fragile in the dry state. On immersion in 1 M hydrochloric acid (to ensure protonation of all the sulfonic acid moieties), and subsequent washing with deionized water, the composite membrane once again became transparent. The wet composite membrane (approximately 100 micron thick) was also strong and flexible.

EXAMPLE 3

Porous Polyethylene Impregnated with a Copolymer of α,β,β-trifluorostyrene, m-trifluoromethyl-α,β,β-trifluorostyrene and p-sulfonyl fluoride-α,β,β-trifluorostyrene, and Subsequent Hydrolysis (Composite Membrane C)

The substrate, a 10 inch×10 inch piece of high density polyethylene (from 3M, product ID #43-9100-6770-1, 81% porosity, approximately 50 micron) was clamped in a frame and immersed in a N,N-dimethylformamide solution (5% w/w) of a copolymer of α,β,β-trifluorostyrene, m-trifluoromethyl-α,β,β-trifluorostyrene and p-sulfonyl fluoride-α,β,β-trifluorostyrene (equivalent weight 480 g/mol after hydrolysis) in a glass container. The container was covered to exclude moisture and particulate contaminants. After 2 hours excess polymer solution was removed and the transparent, wetted substrate was placed to dry in a chamber at approximately 2% relative humidity, at 50° C. After approximately 3 hours the dry composite membrane was a mechanically strong flexible film. The sulfonyl fluoride moieties were hydrolyzed by treatment of the composite membrane with potassium hydroxide solution (approximately 6% w/w, in 5:1 w/w water:1-methoxy-2-propanol) at 60° C. (see U.S. Pat. No. 5,310,765). The composite membrane was then immersed in 1 M hydrochloric acid to ensure protonation of all the sulfonic acid moieties in the composite membrane, and subsequently washed with deionized water. The wet, hydrolyzed composite membrane (50–70 micron thick) was also strong and flexible.

EXAMPLE 4

Expanded Polytetrafluoroethylene Impregnated with a Sulfonated Copolymer of α,β,β-trifluorostyrene and m-trifluoromethyl-α,β,β-trifluorostyrene (Composite Membrane D)

The substrate, an 8 inch×8 inch piece of expanded polytetrafluoroethylene (Tetratex® obtained from Tetratec Corporation, 80–90% porosity, approximately 38 micron, 0.45 micron pore size) was clamped in a frame and immersed in a methanol/propan-2-ol (3:1) solution (approximately 5% w/v) of a sulfonated copolymer of α,β,β-trifluorostyrene and m-trifluoromethyl-α,β,β-trifluorostyrene (equivalent weight 412 g/mol) in a glass container. The container was covered to exclude moisture and particulate contaminants. After 18 hours excess polymer solution was removed and the transparent, wetted substrate was placed to dry in a chamber at approximately 2% relative humidity, at 50° C. After approximately 1.5 hours the dry composite membrane, now opaque, was a mechanically strong flexible film. On immersion in 1 M hydrochloric acid (to ensure protonation of all the sulfonic acid moieties), and subsequent washing with deionized water, the composite membrane once again became transparent. The wet composite membrane (50–60 micron thick) was also strong and flexible.

EXAMPLE 5

Expanded Polytetrafluoroethylene Impregnated with a Sulfonated Copolymer of α,β,β-trifluorostyrene and m-trifluoromethyl-α,β,β-trifluorostyrene (Composite Membrane E)

The composite membrane was prepared as described in Example 4, using a sulfonated copolymer of α,β,β-trifluorostyrene and m-trifluoromethyl-α,β,β-trifluorostyrene with a lower equivalent weight (362 g/mol) and impregnating the substrate for 30 minutes. The resulting dry composite membrane was a mechanically strong flexible film, in contrast to the analogous unsupported membrane which, at this low equivalent weight, is extremely fragile and readily reduced to a powder on handling. The wet composite membrane (25–40 micron thick) was also strong and flexible, again in contrast to the unsupported membrane which is fragile and dimensionally unstable, and is therefore of limited use in electrochemical fuel cells.

EXAMPLE 6

Each of the composite membranes prepared as described above was bonded to two catalyzed carbon fiber paper electrodes at room temperature under 7,500 pounds of pressure. Each membrane electrode assembly was tested in a Ballard Mark IV single cell fuel cell (see U.S. Pat. Nos. 4,988,583; 5,108,849; 5,170,124; 5,176,966 and 5,200,278; all incorporated herein by reference in their entirety). The following operating conditions applied to the fuel cell in which the membranes were tested:

Temperature: 70° C.

Reactant inlet pressure:
  24 psi for both air and hydrogen

Reactant stoichiometries:
  2.0 air and 1.15 hydrogen.

The membrane electrode assemblies incorporating the composite membranes were tested for 200–1400 hours, depending on availability of testing equipment.

Figure 2:
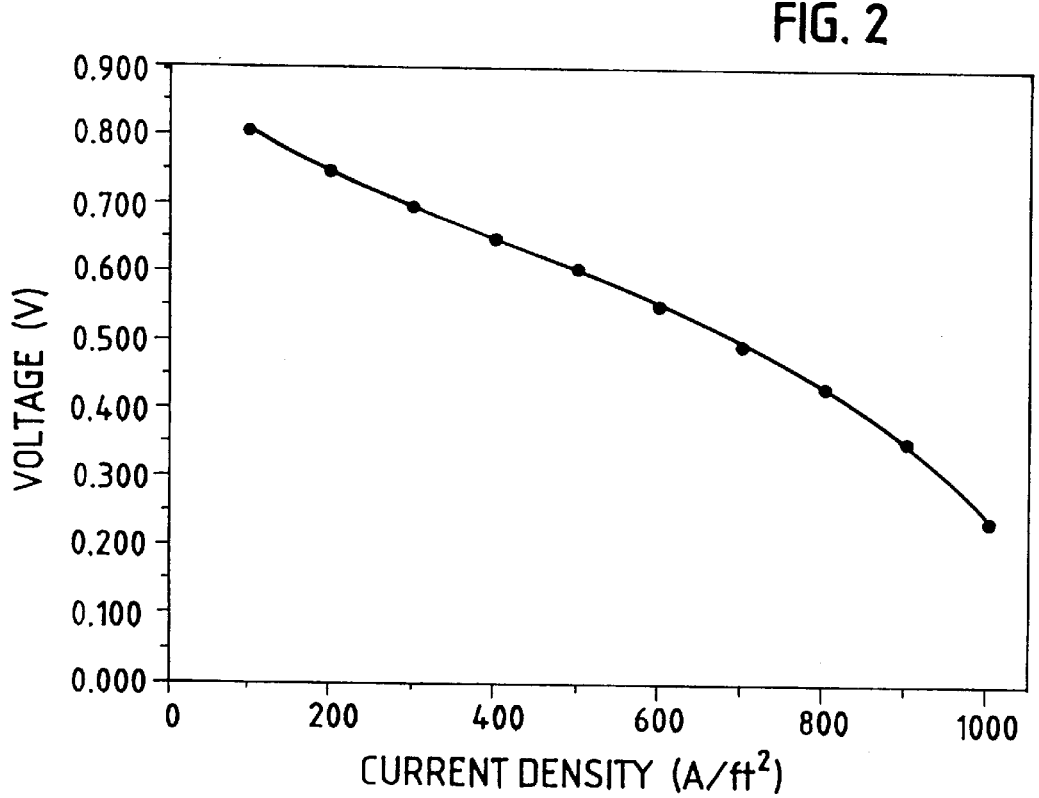
FIG. 2 is a plot of cell voltage as a function of current density in an electrochemical fuel cell employing a composite membrane, prepared by impregnation of porous polyethylene with sulfonated poly-$\alpha,\beta,\beta$-trifluorostyrene, as the proton exchange membrane.
Figure 3:
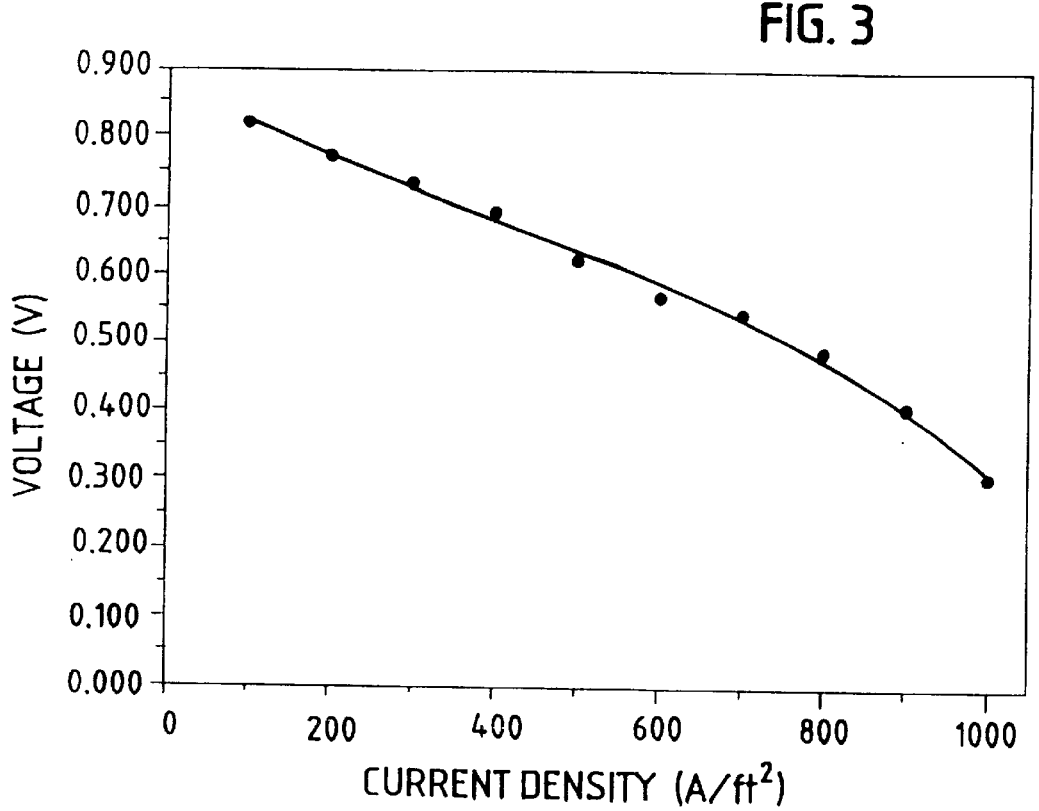
FIG. 3 is a plot of cell voltage as a function of current density in an electrochemical fuel cell employing a composite membrane, prepared by impregnation of porous polyethylene with a copolymer of $\alpha,\beta,\beta$-trifluorostyrene, m-trifluoromethyl-$\alpha,\beta,\beta$-trifluorostyrene and p-sulfonyl fluoride-$\alpha,\beta,\beta$-trifluorostyrene, and subsequent hydrolysis, as the proton exchange membrane.
Figure 4:
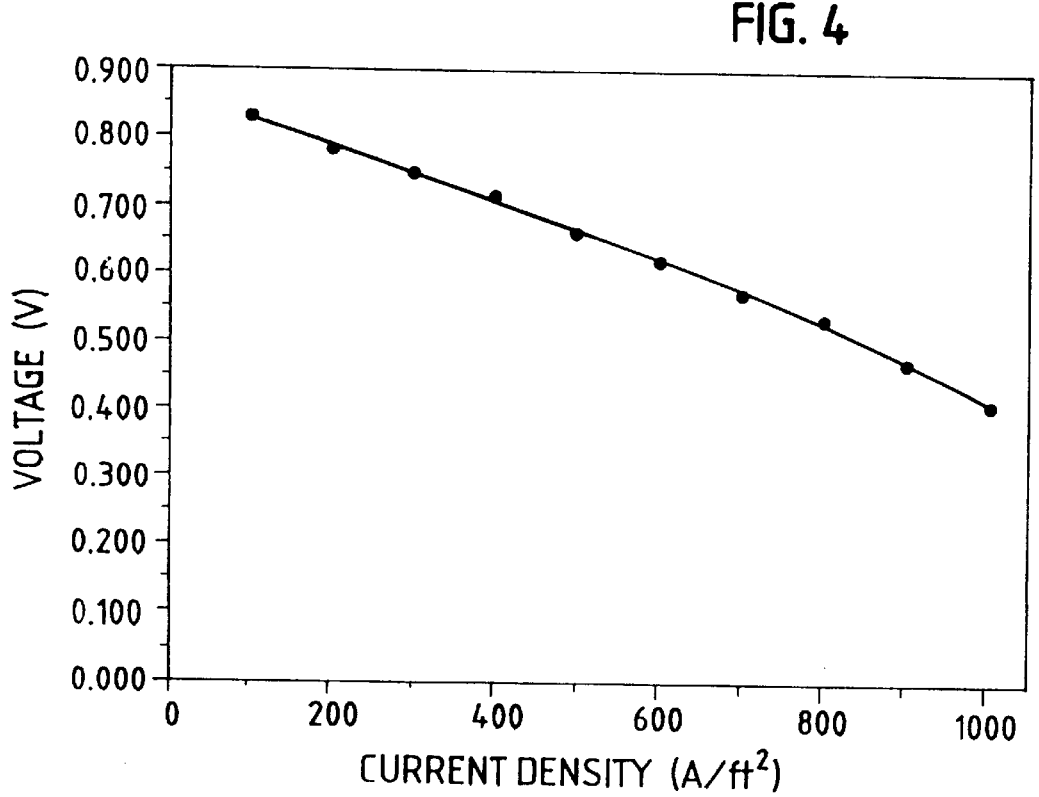
FIG. 4 is a plot of cell voltage as a function of current density in an electrochemical fuel cell employing a composite membrane of expanded polytetrafluoroethylene impregnated with a sulfonated copolymer of $\alpha,\beta,\beta$-trifluorostyrene and m-trifluoromethyl-$\alpha,\beta,\beta$-trifluorostyrene, as the proton exchange membrane.

FIGS. 1–5 are polarization plots of voltage as a function of current density for composite membranes A–E, respectively, employed in membrane electrode assemblies in the electrochemical fuel cell. The data is comparable to data reported for unsupported membranes in related U.S. Pat. No. 5,422,411.

While particular elements, embodiments and applications of the present invention have been shown and described, it will be understood, of course, that the invention is not limited thereto since modifications may be made by those skilled in the art, particularly in light of the foregoing teachings. It is therefore contemplated by the appended claims to cover such modifications as incorporate those features which come within the spirit and scope of the invention.

What is claimed is:

1. A composite membrane that is flexible in the dry state, the composite membrane comprising a flexible porous sheet material impregnated with a polymeric composition consisting predominantly of:

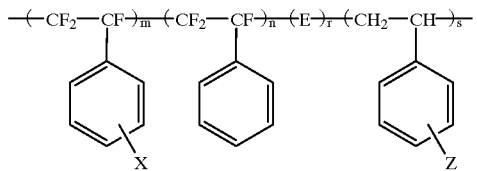

wherein each of m, n, r and s is zero or an integer greater than zero, and at least one of m and n is an integer greater than zero;

X is selected from the group consisting of $SO_3H$, $PO_2H_2$, $PO_3H_2$, $CH_2PO_3H_2$, COOH, $OSO_3H$, $OPO_2H_2$, $OPO_3H_2$, $OArSO_3H$ where Ar is an aryl, $NR_3^+$ (where R is selected from the group consisting of alkyls, perfluoroalkyls and aryls) and $CH_2NR_3^+$ (where R is selected from the group consisting of alkyls, perfluoroalkyls and aryls);

Z is selected from the group consisting of hydrogen, $SO_2F$, halogens, $C_xH_yF_z$ (where x is an integer greater than zero and y+z=2x+1), $SO_3H$, $PO_2H_2$, $PO_3H_2$, $CH_2PO_3H_2$, COOH, $OSO_3H$, $OPO_2H_2$, $OPO_3H_2$, $OArSO_3H$ where Ar is an aryl, $NR_3^+$ (where R is selected from the group consisting of alkyls, perfluoroalkyls and aryls) and $CH_2NR_3^+$ (where R is selected from the group consisting of alkyls, perfluoroalkyls and aryls); and E is selected from the group consisting of $CH_2$—$CH_2$, $CH_2$—CHF, CFH—CFH, $CF_2$—$CH_2$, $CF_2$—CHF, $CF_2$—$CF_2$.

2. A composite membrane according to claim 1 wherein both m and n are integers greater than zero.

3. A composite membrane according to claim 2 wherein X is $SO_2H$.

4. A composite membrane according to claim 2 wherein r and s are zero.

5. A composite membrane according to claim 1 wherein m, n and r are integers greater than zero.

6. A composite membrane according to claim 1 wherein m, n and s are integers greater than zero.

7. A composite membrane according to claim 6 wherein Z is hydrogen.

8. A composite membrane according to claim 1 wherein said flexible porous sheet material is a polymeric sheet material.

9. A composite membrane according to claim 8 wherein said porous polymeric sheet material comprises polytetrafluoroethylene.

10. A composite membrane according to claim 8 wherein said porous polymeric sheet material comprises a polyolefin.

11. A composite membrane according to claim 8 wherein said porous polymeric sheet material comprises a partially fluorinated polyolefin.

12. A composite membrane according to claim 8 wherein said porous polymeric sheet material comprises a polymer selected from the group consisting of polyethylene, polypropylene, polyvinylidene fluoride, poly(ethylene-co-tetrafluoroethylene) and poly(tetrafluoroethylene-co-hexafluoropropylene).

13. A composite membrane according to claim 9, wherein said porous sheet material is expanded polytetrafluoroethylene film.

14. A composite membrane according to claim 1 wherein said composite membrane is substantially gas impermeable.

15. A membrane electrode assembly comprising a composite membrane of claim 14, wherein said composite membrane is an ion-exchange membrane.

16. An electrochemical fuel cell comprising a composite membrane of claim 14, wherein said composite membrane is an ion-exchange membrane.

17. A composite membrane that is flexible in the dry state, the composite membrane comprising a flexible porous sheet material impregnated with a polymeric composition consisting essentially of:

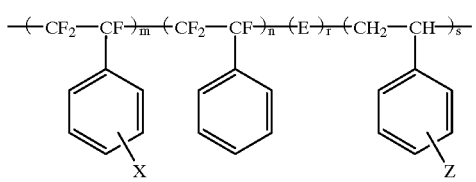

wherein each of m, n, n, r and s is zero or an integer greater than zero, and at least one of m and n is an integer greater than zero;

X is selected from the group consisting of $SO_3H$, $PO_2H_2$, $PO_3H_2$, $CH_2PO_3H_2$, COOH, $OSO_3H$, $OPO_2H_2$, $OPO_3H_2$, $OArSO_3H$ where Ar is an aryl, $NR_3^+$ (where R is selected from the group consisting of alkyls, perfluoroalkyls and aryls) and $CH_2NR_3^+$ (where R is selected from the group consisting of alkyls, perfluoroalkyls and aryls);

Z is selected from the group consisting of hydrogen, $SO_2F$, halogens, $C_xH_yF_z$ (where x is an integer greater than zero and y+z=2x+1), $SO_3H$, $PO_2H_2$, $PO_2H_2$, $CH_2PO_2H_2$, COOH, $OSO_3H$, $OPO_2H_2$, $OPO_3H_2$, OArSO$_2$H where Ar is an aryl, NR$_3{}^+$ (where R is selected from the group consisting of alkyls, perfluoroalkyls and aryls) and CH$_2$NR$_3{}^+$ (where R is selected from the group consisting of alkyls, perfluoroalkyls and aryls); and E is selected from the group consisting of CH$_2$—CH$_2$, CH$_2$—CHF, CFH—CFH, CF$_2$—CH$_2$, CF$_2$—CHF, CF$_2$—CF$_2$.

18. A composite membrane according to claim 17 wherein both m and n are integers greater than zero.

19. A composite membrane according to claim 18 wherein X is SO$_3$H.

20. A composite membrane according to claim 18 wherein r and s are zero.

21. A composite membrane according to claim 17 wherein m, n and r are integers greater than zero.

22. A composite membrane according to claim 17 wherein m, n and s are integers greater than zero.

23. A composite membrane according to claim 22 wherein Z is hydrogen.

24. A composite membrane according to claim 17 wherein said flexible porous sheet material is a polymeric sheet material.

25. A composite membrane according to claim 24 wherein said porous polymeric sheet material comprises polytetrafluoroethylene.

26. A composite membrane according to claim 24 wherein said porous polymeric sheet material comprises a polyolefin.

27. A composite membrane according to claim 24 wherein said porous polymeric sheet material comprises a partially fluorinated polyolefin.

28. A composite membrane according to claim 24 wherein said porous polymeric sheet material comprises a polymer selected from the group consisting of polyethylene, polypropylene, polyvinylidene fluoride, poly(ethylene-co-tetrafluoroethylene) and poly(tetrafluoroethylene-co-hexafluoropropylene).

29. A composite membrane according to claim 25, wherein said porous sheet material is expanded polytetrafluoroethylene film.

30. A composite membrane according to claim 17 wherein said composite membrane is substantially gas impermeable.

31. A membrane electrode assembly comprising a composite membrane of claim 30, wherein said composite membrane is an ion-exchange membrane.

32. An electrochemical fuel cell comprising a composite membrane of claim 30, wherein said composite membrane is an ion-exchange membrane.

* * * * *

UNITED STATES PATENT AND TRADEMARK OFFICE
CERTIFICATE OF CORRECTION

PATENT NO. : 5,985,942

DATED : November 16, 1999

INVENTOR(S) : Alfred E. Steck and Charles Stone

It is certified that error appears in the above-identified patent and that said Letters Patent is hereby corrected as shown below:

At Col. 3, line 52, delete "here" and substitute therefor --where--

At Col. 3, line 57, delete "ON" and substitute therefor --CN--

At Col. 5, line 52, delete " $OPO_3H_{21}$" and substitute therefor -- $OPO_3H_2$, --

At Col. 6, line 51, delete "$PO_2H_{21}$" and substitute therefor --$PO_2H_2$, --

At Col. 6, line 52, delete "$NR_3^-$" and substitute therefor -- $NR_3^+$ --

At Col. 8, line 37, the polymeric composition, delete the third "$CF_2$" and substitute therefor --$CH_2$--

At Col. 16, line 4, claim 3, delete "$SO_2H$" and substitute therefor --$SO_3H$--

UNITED STATES PATENT AND TRADEMARK OFFICE
CERTIFICATE OF CORRECTION

PATENT NO. : 5,985,942

DATED : November 16, 1999

INVENTOR(S) : Alfred E. Steck and Charles Stone

It is certified that error appears in the above-identified patent and that said Letters Patent is hereby corrected as shown below:

At Col. 16, line 66, claim 17, delete the last "$PO_2H_2$" and substitute therefor --$PO_3H_2$,--

At Col. 17, line 1, claim 17, delete "$OArSO_2H$" and substitute therefor --$OArSO_3H$--

Signed and Sealed this

First Day of August, 2000

Attest:

Attesting Officer

Q. TODD DICKINSON

Director of Patents and Trademarks